United States Patent [19]

Plummer

[11] Patent Number: 4,617,316

[45] Date of Patent: Oct. 14, 1986

[54] INSECTICIDAL HETEROARYL SUBSTITUTED PHENYL BENZOYLUREAS

[75] Inventor: Ernest L. Plummer, Yardley, Pa.

[73] Assignee: FMC Corporation, Philadelphia, Pa.

[21] Appl. No.: 811,208

[22] Filed: Dec. 20, 1985

Related U.S. Application Data

[62] Division of Ser. No. 589,604, Mar. 14, 1984.

[51] Int. Cl.[4] ..................... A01N 43/08; A01N 43/10; C07D 307/54; C07D 333/24
[52] U.S. Cl. .................................... 514/438; 514/417; 514/427; 514/471; 548/476; 548/563; 549/77; 549/496
[58] Field of Search .................. 549/77, 496; 514/438, 514/471

[56] References Cited

U.S. PATENT DOCUMENTS 4,560,770 12/1985 Gehret et al. ..................... 548/561

FOREIGN PATENT DOCUMENTS 0060071 9/1982 European Pat. Off. .

OTHER PUBLICATIONS

Veveris et al., Chemical Abstracts, vol. 72, (1970), 132260f.
Chemical Abstracts, 98:71950 u (1983)–Abstract of Japanese Kokai 57,145,861 (Sep. 9, 1982).
Wellinga et al., J. Agr. Food Chem. 21(3), 1973.
Douglass et al., J. Am. Chem. Soc., 56,719 (1934).

*Primary Examiner*—Richard L. Raymond
*Attorney, Agent, or Firm*—William Schmonsees; H. Robinson Ertelt

[57] ABSTRACT

Insecticidal compounds of the formula:

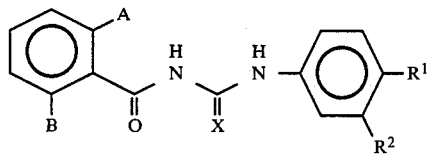

in which A is chloro and B is hydrogen or A and B are both fluoro, X is oxygen or sulfur and one of $R^1$ and $R^2$ is or includes an optionally substituted 5-membered heteroaryl ring, their method for preparation and formulation, insecticidal compositions thereof, and their use to control insects, are disclosed and exemplified.

3 Claims, No Drawings

INSECTICIDAL HETEROARYL SUBSTITUTED PHENYL BENZOYLUREAS

This application is a division of application Ser. No. 589,604 filed Mar. 14, 1984.

The present invention relates to phenyl benzoylureas in which the phenyl ring is substituted with a selected 5-membered heteroaryl ring which may be substituted, to insecticidal compositions, and to a method for controlling insects by disrupting the normal developmental sequence of insects feeding on the compound of the invention.

The present invention thus provides insecticidal compounds of the formula:

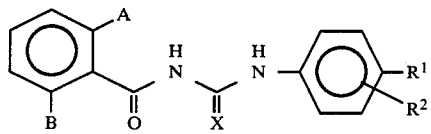

in which:
A. A is chloro, B is hydrogen, X is oxygen, and
(1.) $R^1$ is

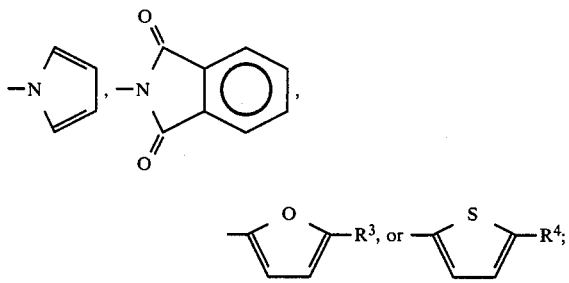

$R^2$ is in the 3-position and is chloro, cyano, alkyl of 1 or 2 carbon atoms, alkoxy of 1 or 2 carbon atoms, or is in the 3- and 5-positions and at each position is a halogen atom; $R^3$ is hydrogen or chloro; $R^4$ is hydrogen or methyl; or
(2.) $R^1$ is hydrogen, halo, alkyl of 1 or 2 carbon atoms, or alkoxy of 1 or 2 carbon atoms; $R^2$ is at the 3-position and is

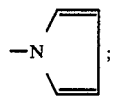

or
B. A is chloro, B is hydrogen, X is sulfur, and
(1.) $R^1$ is

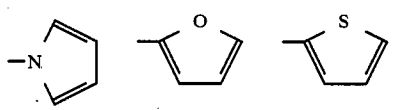

$R^2$ is in the 3-position and is halo, cyano, alkyl of 1 or 2 carbon atoms, alkoxy of 1 or 2 carbon atoms, or halomethyl, with the proviso that $R^1$ is limited to

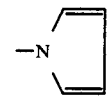

when $R^2$ is chloro; or
(2.) $R^1$ is alkyl of 1 or 2 carbons or alkoxy of 1 or 2 carbon atoms; $R^2$ is in the 3-position and is

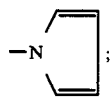

or
C. A and B are each fluoro, X is oxygen; and
(1.) $R^1$ is

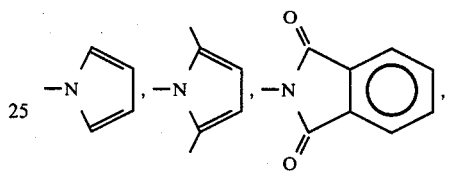

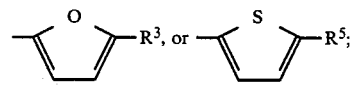

$R^2$ is in the 3-position and is hydrogen, halo, cyano, alkyl of 1 or 2 carbon atoms, alkoxy of 1 to 3 carbon atoms, halomethyl, halomethoxy, or is in the 3- and 5-positions and at each position is a halogen atom; $R^3$ is as defined above and $R^5$ is hydrogen, chloro, methyl, or trifluoromethyl; or
(2.) $R^1$ is hydrogen, halo, alkyl of 1 or 2 carbon atoms, or alkoxy of 1 or 2 carbon atoms; $R^2$ is in the 3-position and is

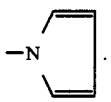

The structures for compounds exemplifying this invention are set forth in and identified by an assigned compound number in Table I below. Characterizing data are provided in Table IA.

The compounds of this invention may be prepared by one of two methods. In the first method described a substituted benzoylisocyanate, which may be prepared by the method set forth in A. J. Speciale, et al., "The Reaction of Oxalyl Chloride with Amides", J. Org. Chem., 10 4306-7 (1965), may be reacted with a substituted heteroarylaniline in xylenes to produce the corresponding N-[[[substituted(heteroaryl)phenyl]amino]-carbonyl]benzamide.

In the second method reported by Douglass and Dains (J. Am. Chem. Soc., 56, 719 (1934), a substituted benzoyl chloride may be reacted with an appropriate substituted heteroaryl aniline and ammonium thiocyanate in acetone to produce the corresponding N-[[[substituted(heteroaryl)phenyl]amino]thioxomethyl]benzamide.

The intermediate heteroarylanilines may be prepared by one or more of the methods set forth in the examples below.

EXAMPLE 1

3-Chloro-4-(1H-pyrrol-1-yl)aniline as an Intermediate

Step A: 1-(2-Chloro-4-nitrophenyl)pyrrole

A stirred mixture of 20.0 g (0.12 mole) of 2-chloro-4-nitroaniline and 17.9 g (0.14 mole) of 2,5-dimethoxytetrahydrofuran in 30 ml of glacial acetic acid was heated at reflux for three hours. The mixture was cooled to room temperature, diluted with water, and extracted with diethyl ether. The extract was washed with a saturated aqueous potassium carbonate solution then dried over anhydrous magnesium sulfate and filtered. The solvent was evaporated from the filtrate under reduced pressure to leave a solid. The solid was purified by recrystallization from methylcyclohexane to yield 22.5 g of 1-(2-chloro-4-nitrophenyl)pyrrole (mp 54°-55° C.).

Step B: 3-Chloro-4-(1H-pyrrol-1-yl)aniline

A stirred mixture of 15.0 g (0.07 mole) of 1-(2-chloro-4-nitrophenyl)pyrrole and 30.0 g (0.53 mole) of iron powder in 100 ml of water was heated at reflux. During a three hour period 59.0 g (0.98 mole) of glacial acetic acid was added dropwise to the refluxing reaction mixture. Reflux was continued for one hour after complete addition. The mixture was cooled to room temperature, filtered and the filter cake rinsed with toluene. The filtrate was extracted with toluene (three 150 ml portions) and the extracts combined with the toluene rinse. The toluene solution was dried over anhydrous magnesium sulfate and filtered. The filtrate was evaporated under reduced pressure to leave an oil which solidified. The solid was purified by column chromatography using silica gel and eluting with methylene chloride, to yield 8.5 g of 3-chloro-4-(pyrrol-1-yl)aniline.

Other anilines prepared by the process of Example 1 were:
3-methoxy-4-(1H-pyrrol-1-yl)aniline;
3,5-diiodo-4-(1H-pyrrol-1-yl)aniline;
4-fluoro-3-(1H-pyrrol-1-yl)aniline;
4-methyl-3-(1H-pyrrol-1-yl)aniline; and
4-methoxy-3-(1H-pyrrol-1-yl)aniline.

EXAMPLE 2

3-Cyano-4-(1H-pyrrol-1-yl)aniline as an Intermediate

Step A: 5-Nitro-2-(1H-pyrrol-1-yl)benzonitrile

In a manner similar to Example 1, Step A, the reaction of 30.0 g (0.18 mole) of 2-amino-5-nitrobenzonitrile with 28.7 g (0.22 mole) of 2,5-dimethoxytetrahydrofuran in 60 ml of glacial acetic acid produced 41.0 g of 5-nitro-2-(1H-pyrrol-1-yl)benzonitrile.

Step B: 3-Cyano-4-(pyrrol-1-yl)aniline

Hydrogenation of 7.0 g (0.03 mole) of 5-nitro-2-(1H-pyrrol-1-yl)benzonitrile with 0.07 g of platinum oxide in 95 ml of methanol produced 6.0 g of 3-cyano-4-(1H-pyrrol-1-yl)aniline.

The nmr and ir spectra were consistent with the proposed structure.

Other anilines prepared by the process of Example 2 were:
4-(1H-pyrrol-1-yl)aniline;
3-methyl-4-(1H-pyrrol-1-yl)aniline;
3-trifluoromethyl-4-(1H-pyrrol-1-yl)aniline;
3-(1H-pyrrol-1-yl)aniline;
4-chloro-3-(1H-pyrrol-1-yl)aniline; and
3-difluoromethoxy-4-(1H-pyrrol-1-yl)aniline.

EXAMPLE 3

3-Ethoxy-4-(1,3-dihydro-1,3-dioxo-2H-isoindol-2-yl)aniline as an Intermediate

Step A: 2-(2-Ethoxy-4-nitrophenyl)-1H-isoindol-1,3(2H)-dione

A stirred mixture of 15.0 g (10.1 mole) of 2-ethoxy-4-nitroaniline and 13.4 g (0.09 mole) of phthalic anhydride in 100 ml of glacial acetic acid was heated at reflux for approximately 18 hours. The reaction mixture was cooled then poured into 700 ml of water to produce a solid which was collected by filtration. The solid was dissolved in methylene chloride, and the resultant solution washed first with an aqueous 10% potassium carbonate solution followed by an aqueous sodium chloride solution. The washed organic solution was dried over anhydrous sodium sulfate, filtered, and the filtrate evaporated under reduced pressure to yield 23.5 g of 2-(2-ethoxy-4-nitrophenyl)-1H-isoindol-1,3-(2H)-dione as a solid (mp 204°-206° C.).

Step B: 3-Ethoxy-4-(1,3-dihydro-1,3-dioxo-2H-isoindol-2-yl)aniline

A stirred mixture of 9.2 g (0.03 mole) of 2-(2-ethoxy-4-nitrophenyl)-1H-isoindol-1,3(2H)-dione and 12.8 g (0.23 mole) of iron powder in 50 ml of water was heated at 100° C. During a two hour period 35.1 g (0.58 mole) of glacial acetic acid was added to the hot reaction mixture. After complete addition the mixture was heated at reflux for four hours. The reaction mixture was cooled then made basic by the addition of potassium carbonate. The basic mixture was extracted with 500 ml of methylene chloride. The extract was filtered, and the filtrate extracted with 300 ml of 2N hydrochloric acid. The acidic extract was made basic with cold concentrated ammonium hydroxide. The basic solution was extracted with methylene chloride. The extract was dried over anhydrous sodium sulfate, filtered, and the filtrate evaporated under the reduced pressure to produce 3.1 g of 3-ethoxy-4-(1,3-dihydro-1,3-dioxo-2H-isoindol-2-yl)aniline as a solid.

The nmr and ir spectra were consistent with the proposed structure.

The process of Example 3 was also used to prepare 4-(1,3-dihydro-1,3-dioxo-2H-isoindol-2-yl)-3-methoxyaniline.

EXAMPLE 4

3-Methoxy-4-(thien-2-yl)aniline as an Intermediate

Step A: 2-(2-Methoxy-4-nitrophenyl)thiophene

A stirred mixture of 38.1 g (0.23 mole) of 2-methoxy-4-nitroaniline and 38.1 g (0.6 mole) of copper powder in 953.0 g (11.33 mole) of thiophene was heated at 55° C. During a 1.1 hour period 40.5 ml (0.34 mole) of t-butylnitrite was added to the warm reaction mixture. After complete addition the mixture was heated at 70° C. for approximately 18 hours then cooled to room temperature. The solvent was removed from the reaction mixture by distillation under reduced pressure to leave a residue. The residue was purified by column chromatography on silica gel, eluting with heptane:toluene (25:75), to yield 29.0 g of 2-(2-methoxy-4-nitrophenyl)thiophene.

Step B: 3-Methoxy-4-(thien-2-yl)aniline

In a manner similar to Example 1, Step B, the reaction of 6.6 g (0.03 mole) of 2-(2-methoxy-4-nitrophenyl)thiophene, 13.65 g (0.24 mole) of iron powder and 25.2 g (0.42 mole) of glacial acetic acid in 36 ml of water produced 5.3 g of 3-methoxy-4-(thien-2-yl)aniline.

Other anilines prepared by the process of Example 4 were:
4-(furan-2-yl)-3-methoxyaniline;
3-chloro-4-(thien-2-yl)aniline;
3-methyl-4-(thien-2-yl)aniline; and
3-methoxy-4-(5-methylthien-2-yl)aniline.

EXAMPLE 5

4-(5-Chlorothien-2-yl)-3-methoxyaniline as an Intermediate

Step A: 2-[4-(Thien-2-yl)-3-methoxyphenyl]-1H-isoindol-1,3(2H)-dione

A stirred mixture of 5.1 g (0.025 mole) of 3-methoxy-4-(thien-2-yl)aniline (prepared in Example 4) and 4.1 g (0.03 mole) of phthalic anhydride in 20 ml of glacial acetic acid was heated at reflux for approximately 18 hours. The hot reaction mixture was poured into 700 ml of distilled water forming a precipitate. The precipitate was collected by filtration and the filter cake dissolved in methylene chloride. The methylene chloride solution was washed first with a 10% aqueous potassium carbonate solution and then with an aqueous sodium chloride solution. The washed organic solution was dried over anhydrous sodium sulfate and filtered. The solvent was removed from the filtrate by evaporation under reduced pressure to yield 8.2 g of 2-[4-thien-2-yl)-3-methoxyphenyl]-1H-isoindol-1,3-(2H)-dione as a solid (mp 153°–155° C.).

Step B: 2-[4-(5-Chlorothien-2-yl)-3-methoxyphenyl]-1H-isoindol-1,3(2H)-dione

In a manner similar to Gilman and Avakian, J. Am. Chem. Soc., 68, 1514 (1946), the chlorination of 5.0 g (0.015 mole) of 2-[4-(thien-2-yl)-3-methoxyphenyl]-1H-isoindol-1,3(2H)-dione with 2.1 g (0.016 mole) of sulfuryl chloride in 90 ml of chloroform produced 5.7 g of a solid residue. The solid was triturated in toluene to yield 3.3 g of 2-[4-(5-chlorothien-2-yl)-3-methoxyphenyl]-1H-isoindol-1,3(2H)-dione (mp 194°–195° C.).

Step C: 4-(5-Chlorothien-2-yl)-3-methoxyaniline

A stirred mixture of 2.5 g (0.007 mole) of 2-[4-(5-chlorothien-2-yl)-3-methoxyphenyl]-1H-isoindol-1,3(2H)-dione and 0.4 g (0.007 mole) of hydrazine hydrate in 30 ml of absolute ethanol was heated at reflux for one hour. The mixture was cooled and the solvent evaporated under reduced pressure to leave a residue. The residue was subjected to column chromatography on silica gel, eluting with methylene chloride to yield 1.4 g of 4-(5-chlorothien-2-yl)-3-methoxyaniline.

The nmr and ir spectra were consistent with the proposed structure.

The process of Example 5 was also used to prepare 4-(5-chlorofuran-2-yl)-3-methoxyaniline.

EXAMPLE 6

3-(2-Methylethoxy)-4-(1H-pyrrol-1-yl)aniline as an Intermediate

Step A: 5-Nitro-2-(1H-pyrrol-1-yl)phenol

In a manner similar to Example 1, Step A, the reaction of 10.0 g (0.06 mole) of 5-nitro-2-aminophenol with 9.8 g (0.07 mole) of 2,5-dimethoxytetrahydrofuran in 20 ml of glacial acetic acid produced 5.5 g of 5-nitro-2-(1H-pyrrol-1-yl)phenol.

Step B: 1-(1-Methylethoxy-4-nitrophenyl)pyrrole

To a stirred mixture of 3.6 g (0.02 mole) of 5-nitro-2-(1H-pyrrol-1-yl)phenol and 3.7 g (0.27 mole) of potassium carbonate in 40 ml of acetone was added 4.5 g (0.027 mole) of 2-iodopropane. After complete addition the mixture was stirred at reflux for approximately 16 hours. The reaction mixture was cooled, and the solvent evaporated under reduced pressure to leave a residue. The residue was dissolved in methylene chloride, filtered, and the filtrate evaporated under reduced pressure to leave residue. The residue was purified by column chromatography on silica gel, eluting with toluene, to yield 3.5 g of 1-(1-methylethoxy-4-nitrophenyl)pyrrole (mp 59°–61° C.).

Step C: 3-(1-Methylethoxy)-4-(1H-pyrrol-1-yl)aniline

In a manner similar to Example 2, Step B, the hydrogenation of 2.7 g (0.011 mole) of 1-(1-methylethoxy-4-nitrophenyl)pyrrole in the presence of 0.03 g of platinum oxide in 35 ml of methanol produced 2.4 g of 3-(1-methylethoxy)-4-(1H-pyrrol-1-yl)aniline (mp 55°–57° C.).

The nmr and ir spectra were consistent with the proposed structure.

EXAMPLE 7

4-(2,5-Dimethyl-1H-pyrrol-1-yl)-3-methoxyaniline as an Intermediate

Step A: 2,5-Dimethyl-1-(2-methoxy-4-nitrophenyl)pyrrole

A stirred mixture of 29.0 g (0.17 mole) of 2-methoxy-4-nitroaniline, 18.7 g (0.16 mole) of acetonylacetone and 0.5 g (0.0026 mole) of p-toluenesulfonic acid in 300 ml of toluene was heated at reflux for two hours. A Dean-Stark trap was used to collect a calculated volume of water. The reaction mixture was cooled then poured into 250 ml of ice water. To the mixture was added 100 ml 2N hydrochloric acid. The organic phase was separated and washed in succession with 100 ml of 2N hydrochloric acid, 100 ml of saturated aqueous sodium chloride, 100 ml of 5% aqueous sodium bicarbonate and 100 ml of saturated aqueous sodium chloride. The washed organic phase was dried over anhydrous sodium sulfate, filtered, and the filtrate evaporated under reduced pressure to yield 39.1 g of 2,5-dimethyl-1-(2-methoxy-4-nitrophenyl)pyrrole.

Step B: 4-(2,5-Dimethyl-1H-pyrrol-1-yl)-3-methoxyaniline

The hydrogenation of 10.0 g (0.04 mole) of 2,5-dimethyl-1-(2-methoxy-4-nitrophenyl)pyrrole in the presence of 0.1 g of platinum oxide in 135 ml of methanol produced 8.7 g of 4-(2,5-dimethyl-1H-pyrrol-1-yl)-3-methoxyaniline.

The nmr and ir spectra were consistent with the proposed structure.

EXAMPLE 8

3-Methoxy-4-(5-trifluoromethylthien-2-yl)aniline as an Intermediate

Step A: 2-Bromo-5-(2-methoxy-4-nitrophenyl)thiophene

To a stirred 0° C. mixture of 8.0 g (0.034 mole) of 2-(2-methoxy-4-nitrophenyl)thiophene (Example 4, Step A) in 180 ml of diethyl ether was added a mixture of 10.8 g (0.07 mole) of bromine in 15.0 ml of 1,4-dioxane and 20 ml of diethyl ether. The mixture was allowed to warm to room temperature and stir for approximately 18 hours. The reaction mixture was poured into a mixture of sodium sulfite and ice water. The resultant mixture was extracted with diethyl ether, and the extract dried over anhydrous sodium sulfate. The dried extract was filtered, and the solvent evaporated from the filtrate to leave a residue. The residue was purified by column chromatography using silica gel and eluting with toluene to yield 9.7 g of 2-bromo-5-(2-methoxy-4-nitrophenyl)thiophene.

Step B: 2-(2-Methoxy-4-nitrophenyl)-5-trifluoromethylthiophene

A stirred solution of 8.0 g (0.026 mole) of 2-bromo-5-(2-methoxy-4-nitrophenyl)thiophene, 13.9 g (0.1 mole) of sodium trifluoroacetate and 9.7 g (0.05 mole) of copper(I)iodide in 160 ml of dry N,N-dimethylacetamide was heated at 175° C. for four hours. The reaction mixture was cooled to room temperature then poured into 400 ml of 2N hydrochloric acid and ice (approximately 1:1). Methylene chloride was added and the resultant mixture filtered. The filtrate separated into two phases. The organic phase was separated then washed with three portions of 2N hydrochloric acid and one portion of water. The washed organic phase was dried over anhydrous sodium sulfate, filtered, and the filtrate evaporated to leave a residue. The residue was subjected to column chromatography on silica gel, eluting with toluene, to yield 1.8 g of a mixture of 2-(2-methoxy-4-nitrophenyl)-5-trifluoromethylthiophene and 2-(2-methoxy-4-nitrophenyl)thiophene.

Step C: 3-Methoxy-4-(5-trifluoromethylthien-2-yl)aniline

In a manner similar to Example 1, Step B, 1.8 g of the mixture from Step B above was treated with 2.9 g (0.05 mole) of iron powder in 7.1 g (0.12 mole) of glacial acetic acid and 9.7 ml of water to produce 2.1 g of an oil. The oil was purified by column chromatography on silica gel, eluting with methylene chloride, to yield 0.3 g of 3-methoxy-4-(5-trifluoromethylthien-2-yl)aniline.

The nmr spectrum was consistent with the proposed structure.

EXAMPLE 9

2-Chloro-N-[[[3-chloro-4-(1H-pyrrol-1-yl)phenyl]amino]carbonyl]benzamide

A stirred mixture of 1.1 g (0.007 mole) of 2-chlorobenzoylisocyanate and 1.00 g (0.005 mole) of 3-chloro-4-(1H-pyrroll-1-yl)aniline (Example 1) in 100 ml of xylenes was heated at reflux for 15 minutes. The mixture was cooled to room temperature forming a precipitate. The precipitate was collected by filtration and rinsed with cold heptane to yield 1.9 g of 2-chloro-N-[[[3-chloro-4-(1H-pyrrol-1-yl)phenyl]amino]carbonyl]benzamide (mp 169°–170° C.).

The compound of Example 9 is listed in Table I as compound 1. Compounds 2–42 were also prepared from the appropriately substituted aniline and 2-chlorobenzoylisocyanate or 2,6-difluorobenzoylisocyanate by using the process described in Example 9.

EXAMPLE 10

2-Chloro-N-[[[3-methyl-4-(1H-pyrrol-1-yl)phenyl]amino]thioxomethyl]benzamide

In a manner similar to Douglas and Dains, J. Am. Chem. Soc., 56, 719 (1934), the reaction of 3.1 g (0.017 mole) of 2-chlorobenzoyl chloride with 1.3 g (0.017 mole) of ammonium thiocyanate and 3.0 g (0.017 mole) of 3-methyl-4-(1H-pyrrol-1-yl)aniline (compound of Example 2) in 100 ml of acetone produced 6.0 g of 2-chloro-N-[[[3-methyl-4-(1H-pyrrol-1-yl)phenyl]amino]thioxomethyl]benzamide (mp 134°–136° C.).

The compound of Example 10 is listed in Table I as Compound 45. Compounds 43, 44 and 46–55 were prepared from the appropriately substituted aniline and 2-chlorobenzoyl chloride or 2-methylbenzoyl chloride by using the process described in Example 10.

The compounds of this invention were tested by incorporating the compounds into the diet of the test insects, second instar southern armyworms and cabbage loopers. The tests were conducted at rates of 200, 20, and 2 ppm, using ten larvae per replicate and two replicates per rate. Each test was read one day, three to four days, and seven to ten days after infestation to determine the number dead after at least one molt.

The test media consisted of a microcrystalline cellulose or clay formation (dust) of the test compound mixed with the insect diet. The formulations of each component of the test media and their method of preparation are:

| Composition of Insect Diet | |
|---|---|
| | parts by weight |
| Pinto beans | 12.90 |
| Wheat germ | 5.68 |
| Brewer's dried yeast | 3.64 |
| Ascorbic acid | 0.37 |
| Methyl paraben | 0.23 |
| Sorbic acid | 0.11 |
| Sodium benzoate | 0.00284 |
| Agar | 0.71 |
| Formalin (40%) | 0.23 |
| Water | 76.13 |

The agar was dissolved with heating in one-half the water and was brought to a boil. Simultaneously, all other ingredients except the formalin were placed in a blender with remaining water and were reduced to a smooth, homogeneous mixture. This mixture was added to the boiling agar. Immediately, the formalin was added with mixing.

The compounds of this invention were formulated as either 20%, 5% or 1% dusts on a microcrystalline cellulose or clay base. The dusts consisted of the following:

| | % w/w | | |
|---|---|---|---|
| Microcrystalline Cellulose Formulation | | 20% Dust | 5% Dust |
| Test compound | | 20.00 | 5.00 |
| Microcrystalline cellulose | | 80.00 | 95.00 |
| | | 100.00 | 100.00 |
| Clay Formulation | 20% Dust | 5% Dust | 1% Dust |
| Test compound | 20.00 | 5.00 | 1.00 |
| Base | 80.00 | 95.00 | 99.00 |
| 96% Attaclay | | | |
| 2% Highly purified sodium ligno-sulfonate (100%) | | | |
| 2% Powdered sodium alkylnaphthalene sulfonate (75%) | | | |
| | 100.00 | 100.00 | 100.00 |

These formulations were prepared by mixing the active ingredient (i.e. the test compound) with the dry base.

Test media containing 200 ppm of the test compound was prepared by making a 'stock solution' from 250 mg of a 20% dust formulation stirred well with 5 ml of distilled water in a vial. One milliliter of the 'stock solution' was added to 50 ml of warm, i.e. molten, insect diet in a plastic petrie dish which was then mixed thoroughly. After cooling to room temperature, the test media was infested with test larvae and covered.

Lower test rates were prepared by dilution of the 'stock solution' according to the following table:

| Desired Rate (ppm) | ml of 'stock solution' | ml of water |
|---|---|---|
| 20 | 1 | 9 |
| 2 | 1 ml of 20 ppm solution | 9 |

The results of diet incorporated testing are summarized in Table II.

The insecticides of this invention, like most agricultural chemicals, are generally not applied full strength, but are formulated with agriculturally acceptable carriers normally employed for facilitating the dispersion of active ingredients, various additives, and optionally with other active ingredients, recognizing that the formulation and mode of application of a toxicant may affect the activity of the material. The present compounds may be applied, for example, as powders or liquids, the choice of application varying with the species and environmental factors present at the particular locus of infestation. Thus, the compounds may be formulated as granules, as dusts, as wettable powders, as emulsifiable concentrates, as solutions, as dispersions, as controlled release compositions, and the like.

A typical formulation may vary widely in concentration of the active ingredient depending on the particular agent used, the additives, carriers, or other active ingredients used, and the desired mode of application. With due consideration to these factors, the active ingredient of a typical formulation may, for example, be suitably present at a concentration of from about 0.5% up to about 99.5% by weight of the formulation. Substantially inactive ingredients such as adjuvants, diluents, and carriers may comprise from about 99.5% by weight to as low as about 0.5% by weight of the formulation. Surface active agents, if employed in the formulation, may be present at various concentrations, suitably in the range of 1 to 30% by weight. Provided below is a general description of exemplary types of formulations which may be employed for the compounds of the present invention.

Dusts are admixtures of the active ingredient with finely divided solid carriers and/or diluents such as talc, natural clays, kieselguhr, pyrophyllite, chalk, diatomaceous earths, calcium phosphates, calcium and magnesium carbonates, sulfur, lime, flours, and other organic and inorganic solid carriers. These finely divided formulations generally have an average particle size of less than about 50 microns (325 mesh, Standard U.S. Sieve Series). In most cases, the active ingredient will be present in dust formulations at a concentration in the range of 1 to 15%, and occasionally from 1% to about 30%, the balance of the composition typically comprising one or more agriculturally acceptable inerts as adjuvant, carrier, or diluent.

Wettable powders, also useful formulations for these compounds, are in the form of finely divided particles which disperse readily in water or other liquid vehicles. The wettable powder is ultimately applied as a dry dust or a dispersion in water or other liquid. Typical carriers for wettable powders include fuller's earth, kaolin clays, silicas, and other highly absorbent or adsorbent inorganic diluents. The concentration of active ingredient in wettable powders is dependent upon physical properties of the active ingredient and the absorbency characteristics of the carrier. Liquids and low melting solids (mp less than 100° C.) are suitably formulated in the concentration range of 5 to 50% by weight; usually 10 to 30%; high melting solids (mp greater than 100° C.) being formulated in the range of 5 to 95% by weight, usually 50 to 85%. An agriculturally acceptable carrier or diluent, frequently including a small amount of a surfactant to facilitate wetting dispersion and suspension, accounts for the balance of the formulation.

Microencapsulated or other controlled release formulations may also be used with the compounds of this invention.

Emulsifiable concentrates (EC's) are homogeneous liquid compositions, usually containing the active ingredient dissolved in a liquid carrier. Commonly used liquid carriers include xylene, heavy aromatic naphthas, isophorone, and other nonvolatile or slightly volatile organic solvents. For application of the compounds, these concentrates are dispersed in water, or other liquid vehicle, forming an emulsion, and are normally applied as a spray to the area to be treated. The concentration of the essential active ingredient in EC's may vary according to the manner in which the composition is to be applied, but, in general, is in the range of 0.5 to 95%, frequently 10 to 80%, by weight of active ingredient, with the remaining 99.5% to 5% being sufactant and liquid carrier.

Flowables are similar to EC's except that the ingredient is suspended in a liquid carrier, generally water or a nonvolatile organic liquid such as aromatic or aliphatic hydrocarbons, vegetable oil or a mineral oil. Flowables, like EC's, may include a small amount of a surfactant, and contain active ingredient in the range of 0.5 to 95%, frequently from 10 to 50%, by weight of the composition. For application, flowables may be diluted in water or other liquid vehicle, and are normally applied as a spray to the area to be treated.

Typical wetting, dispersing or emulsifying agents used in formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. The surface-active agent, when used, normally comprises from 1 to 15% by weight of the composition.

Other useful formulations include simple solutions of the active ingredient in a relatively non-volatile solvent such as corn oil, kerosene, propylene glycol, or other organic solvents. This type of formulation is particularly useful for ultra low volume application.

The concentration of the active ingredient in use dilution is normally in the range of about 2% to about 0.1%. Many variations of spraying, dusting, and controlled or slow release compositions in the art may be used by substituting or adding a compound of this invention into compositions known or apparent to the art.

These compositions may be formulated and applied with other suitable active ingredients, including nematicides, insecticides, acaricides, fungicides, plant regulators, herbicides, fertilizers, etc.

In applying the foregoing chemicals, an effective insecticidal controlling amount of active ingredient must be applied, sometimes referred to herein as an insecticidal amount. While the application rate will vary widely depending on the choice of compound, the formulation and mode of application, the plant species being protected and the planting density, a suitable use rate may be in the range of 75 to 4000 g per hectare, preferably 150 g to about 3000 kg/hectare.

The compounds of this invention are usually applied by incorporating or applying formulation thereof to a food source for the insects to be controlled, i.e. the locus where control is required, including application to the above ground portions of plants on which the insects feed or in a bait-type formulation for application to surfaces on which insects normally do not feed. The compounds may also be applied to the soil in which plants are or are about to be planted in order to provide control of soil-borne insects.

TABLE 1

Heteroaryl Substituted Phenyl Benzoylureas

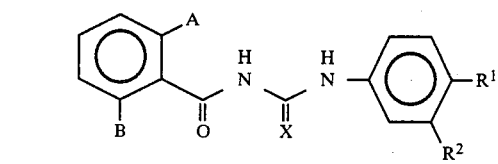

| Cmpd. No. | A | B | X | R¹ | R² |
|---|---|---|---|---|---|
| 1 | Cl | H | O | —N (pyrrole) | Cl |
| 2 | Cl | H | O | " | CN |
| 3 | Cl | H | O | " | CH₃ |
| 4 | Cl | H | O | " | OCH₃ |
| 5 | Cl | H | O | " | I* |
| 6 | Cl | H | O | " | OCH₃ |
| 7 | Cl | H | O | " | OC₂H₅ |
| 8 | Cl | H | O | H | —N (pyrrole) |
| 9 | Cl | H | O | F | " |
| 10 | Cl | H | O | Cl | " |
| 11 | Cl | H | O | CH₃ | " |
| 12 | Cl | H | O | OCH₃ | " |
| 13 | Cl | H | O | (furan) | OCH₃ |
| 14 | Cl | H | O | (5-Cl-furan) | OCH₃ |
| 15 | Cl | H | O | (thiophene) | OCH₃ |
| 16 | Cl | H | O | (5-CH₃-thiophene) | OCH₃ |

TABLE 1-continued

Heteroaryl Substituted Phenyl Benzoylureas

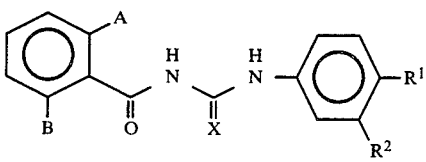

| Cmpd. No. | A | B | X | R¹ | R² |
|---|---|---|---|---|---|
| 17 | F | F | O | —N (pyrrole) | H |
| 18 | F | F | O | " | Cl |
| 19 | F | F | O | " | CN |
| 20 | F | F | O | " | CH₃ |
| 21 | F | F | O | " | CF₃ |
| 22 | F | F | O | " | OCH₃ |
| 23 | F | F | O | " | OCHF₂ |
| 24 | F | F | O | " | OCH₂(CH₃)₂ |
| 25 | F | F | O | " | I* |
| 26 | F | F | O | (2,5-dimethylpyrrole) | OCH₃ |
| 27 | F | F | O | " | OC₂H₅ |
| 28 | F | F | O | (phthalimide) | OCH₃ |
| 29 | F | F | O | (phthalimide) | OC₂H₅ |
| 30 | F | F | O | H | —N (pyrrole) |
| 31 | F | F | O | F | —N (pyrrole) |
| 32 | F | F | O | Cl | " |
| 33 | F | F | O | CH₃ | " |
| 34 | F | F | O | OCH₃ | " |
| 35 | F | F | O | (furan) | OCH₃ |
| 36 | F | F | O | (5-Cl-furan) | OCH₃ |

TABLE 1-continued

Heteroaryl Substituted Phenyl Benzoylureas

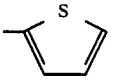

| Cmpd. No. | A | B | X | R¹ | R² |
|---|---|---|---|---|---|
| 37 | F | F | O | 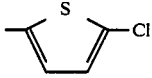 | Cl |
| 38 | F | F | O | " | CH₃ |
| 39 | F | F | O | " | OCH₃ |
| 40 | F | F | O | 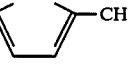 | OCH₃ |
| 41 | F | F | O | 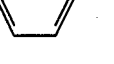 | OCH₃ |
| 42 | F | F | O | 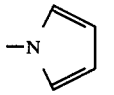 | OCH₃ |
| 43 | Cl | H | S | 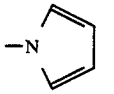 | Cl |
| 44 | Cl | H | S | " | CN |
| 45 | Cl | H | S | " | CH₃ |
| 46 | Cl | H | S | " | CF₃ |
| 47 | Cl | H | S | " | OCH₃ |
| 48 | Cl | H | S | " | OCHF₂ |
| 49 | Cl | H | S | 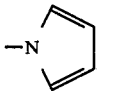 | OC₂H₅ |
| 50 | Cl | H | S | CH₃ |  |
| 51 | Cl | H | S | OCH₃ | " |
| 52 | Cl | H | S | 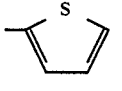 | OCH₃ |
| 53 | Cl | H | S | 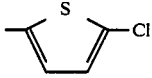 | H |
| 54 | Cl | H | S | " | CH₃ |
| 55 | Cl | H | S | " | OCH₃ |

*In each of positions 3 and 5.

TABLE 1A

| Cmpd No. | mp (°C.) | Empirical Formula | C/F* | C | H |
|---|---|---|---|---|---|
| 1 | 169-170 | C₁₈H₁₃Cl₂N₃O₂ | C | 57.77 | 3.50 |
|   |         |                 | F | 59.43 | 3.54 |
| 2 | 189-191 | C₁₉H₁₃ClN₄O₂ | C | 62.56 | 3.59 |
|   |         |                | F | 61.62 | 3.48 |
| 3 | 160-162 | C₁₉H₁₉ClN₃O₂ | C | 64.50 | 4.56 |
|   |         |                | F | 64.30 | 4.40 |
| 4 | 159-160 | C₁₉H₁₆ClN₃O₃ | C | 61.71 | 4.36 |
|   |         |                | F | 62.14 | 4.20 |
| 5 | 264-266 | C₁₈H₁₂ClIN₃O₂ | C | 36.55 | 2.05 |
|   |         |                 | F | 37.24 | 2.27 |
| 6 | 168-170 | C₂₃H₁₆ClN₃O₅ | C | 61.41 | 3.59 |
|   |         |                | F | 60.50 | 3.55 |
| 7 | 150-152 | C₂₄H₁₈ClN₃O₅ | C | 62.14 | 3.91 |
|   |         |                | F | 60.29 | 3.85 |
| 8 | 135-137 | C₁₈H₁₄ClN₃O₂ | C | 63.63 | 4.15 |
|   |         |                | F | 63.47 | 4.02 |
| 9 | 154-156 | C₁₈H₁₃ClFN₃O₂ | C | 60.43 | 3.66 |
|   |         |                  | F | 60.41 | 3.49 |
| 10 | 140-142 | C₁₈H₁₃Cl₂N₃O₂ | C | 57.77 | 3.50 |
|    |         |                  | F | 57.88 | 3.44 |
| 11 | 162-163 | C₁₉H₁₆ClN₃O₂ | C | 64.50 | 4.56 |
|    |         |                 | F | 64.81 | 4.37 |
| 12 | 170-172 | C₁₉H₁₆ClN₃O₃ | C | 61.71 | 4.36 |
|    |         |                 | F | 61.68 | 4.37 |
| 13 | 192-194 | C₁₉H₁₅ClN₂O₄ | C | 61.54 | 4.08 |
|    |         |                 | F | 61.91 | 4.44 |
| 14 | 175-177 | C₁₈H₁₄Cl₂N₂O₄ | C | 54.98 | 3.59 |
|    |         |                  | F | 57.24 | 3.51 |
| 15 | 155 | C₁₉H₁₅ClN₂O₃S | C | 58.99 | 3.91 |
|    |     |                  | F | 59.15 | 3.81 |
| 16 | 148-150 | C₂₀H₁₇ClN₂O₃S | C | 59.92 | 4.27 |
|    |         |                  | F | 56.62 | 4.10 |
| 17 | 244-245 | C₁₈H₁₃F₂N₃O₂ | C | 63.34 | 3.84 |
|    |         |                 | F | 62.99 | 3.71 |
| 18 | 224-225.5 | C₁₈H₁₂ClF₂N₃O₂ | C | 57.54 | 3.22 |
|    |           |                    | F | 57.06 | 3.04 |
| 19 | 231-233 | C₁₉H₁₂F₂N₄O₂ | C | 62.30 | 3.30 |
|    |         |                 | F | 61.94 | 3.17 |
| 20 | 236-237 | C₁₉H₁₅F₂N₃O₂ | C | 64.22 | 4.26 |
|    |         |                 | F | 64.88 | 4.33 |
| 21 | 226-227 | C₁₉H₁₂F₅N₃O₂ | C | 55.75 | 2.96 |
|    |         |                 | F | 54.88 | 3.18 |
| 22 | 212-214 | C₁₉H₁₅F₂N₃O₃ | C | 61.46 | 4.07 |
|    |         |                 | F | 61.38 | 4.06 |
| 23 | 172-173 | C₁₉H₁₃F₄N₃O₃ | C | 56.03 | 3.22 |
|    |         |                 | F | 56.14 | 3.00 |
| 24 | 116-118 | C₂₁H₁₉F₂N₃O₃ | C | 63.15 | 4.80 |
|    |         |                 | F | 61.20 | 4.50 |
| 25 | 272-274 | C₁₈H₁₁F₂I₂N₃O₂ | C | 36.45 | 1.87 |
|    |         |                    | F | 36.77 | 2.05 |
| 26 | 115-117 | C₂₁H₁₉F₂N₃O₃ | C | 63.15 | 4.80 |
|    |         |                 | F | 62.61 | 5.06 |
| 27 | 142-143 | C₂₂H₂₁F₂N₃O₃ | C | 63.92 | 5.12 |
|    |         |                 | F | 62.35 | 4.80 |
| 28 | 231-232 | C₂₃H₁₅F₂N₃O₅ | C | 61.20 | 3.35 |
|    |         |                 | F | 60.56 | 3.19 |
| 29 | 196-198 | C₂₄H₁₇F₂N₃O₅ | C | 61.94 | 3.68 |
|    |         |                 | F | 61.50 | 3.72 |
| 30 | 192-194 | C₁₈H₁₃F₂N₃O₂ | C | 63.34 | 3.84 |
|    |         |                 | F | 63.62 | 3.70 |
| 31 | 210-211 | C₁₈H₁₂F₃N₃O₂ | C | 60.17 | 3.37 |
|    |         |                 | F | 60.09 | 3.22 |
| 32 | 204-205 | C₁₈H₁₂ClF₂N₃O₂ | C | 57.54 | 3.22 |
|    |         |                   | F | 56.71 | 3.55 |
| 33 | 211-213 | C₁₉H₁₅F₂N₃O₂ | C | 64.22 | 4.26 |
|    |         |                 | F | 64.49 | 4.51 |
| 34 | 212-214 | C₁₉H₁₄F₂N₃O₃ | C | 61.46 | 4.07 |
|    |         |                 | F | 61.56 | 4.40 |
| 35 | 181-183 | C₁₉H₁₄F₂N₂O₄ | C | 61.29 | 3.79 |
|    |         |                 | F | 59.98 | 4.11 |
| 36 | 180-183 | C₁₈H₁₃ClF₂N₂O₄ | C | 54.77 | 3.32 |
|    |         |                    | F | 56.57 | 3.24 |
| 37 | 204-206 | C₁₈H₁₁ClF₂N₂O₂S | C | 55.04 | 2.82 |
|    |         |                     | F | 54.98 | 2.79 |
| 38 | 216-220 | C₁₉H₁₄F₂N₂O₂S | C | 61.28 | 3.79 |
|    |         |                    | F | 60.60 | 4.07 |
| 39 | 189.4-190.5 | C₁₉H₁₄F₂N₂O₃S | C | 58.76 | 3.63 |
|    |             |                    | F | 58.76 | 3.46 |

TABLE 1A-continued

| Cmpd No. | mp (°C.) | Empirical Formula | C/F* | C | H |
|---|---|---|---|---|---|
| 40 | 238–240 | C₁₉H₁₃ClF₂N₂O₃S | C | 53.97 | 3.10 |
|  |  |  | F | 51.55 | 3.29 |
| 41 | 170–172 | C₂₀H₁₆F₂N₂O₃S | C | 59.69 | 4.01 |
|  |  |  | F | 43.85 | 3.89 |
| 42 | 215–217 | C₂₀H₁₃F₅N₂O₃S | C | 52.63 | 2.87 |
|  |  |  | F | 49.59 | 2.88 |
| 43 | 140–141 | C₁₈H₁₃Cl₂N₃OS | C | 55.39 | 3.36 |
|  |  |  | F | 55.05 | 3.48 |
| 44 | 169–171 | C₁₉H₁₃ClN₄OS | C | 59.92 | 3.44 |
|  |  |  | F | 60.21 | 3.40 |
| 45 | 134–136 | C₁₉H₁₆ClN₃OS | C | 61.70 | 4.36 |
|  |  |  | F | 62.30 | 4.49 |
| 46 | 115–117 | C₁₉H₁₃ClF₃N₃OS | C | 53.84 | 3.09 |
|  |  |  | F | 54.56 | 2.94 |
| 47 | 106–108 | C₁₉H₁₆ClN₃O₂S | C | 59.14 | 4.18 |
|  |  |  | F | 60.15 | 4.35 |
| 48 | 149–151 | C₁₉H₁₄ClF₂N₃O₂S | C | 54.10 | 3.35 |
|  |  |  | F | 54.50 | 3.29 |
| 49 | 180–182 | C₂₄H₁₈ClN₃O₄S | C | 60.06 | 3.78 |
|  |  |  | F | 59.69 | 3.76 |
| 50 | 171–172 | C₁₉H₁₆ClN₃OS | C | 61.69 | 4.36 |
|  |  |  | F | 61.50 | 4.31 |
| 51 | 152–154 | C₁₉H₁₆ClN₃O₂S | C | 59.14 | 4.18 |
|  |  |  | F | 59.13 | 4.04 |
| 52 | 163–165 | C₁₉H₁₅ClN₂O₃S | C | 60.94 | 4.04 |
|  |  |  | F | 59.13 | 4.49 |
| 53 | 128–130 | C₁₈H₁₃ClN₂OS₂ | C | 57.98 | 3.51 |
|  |  |  | F | 57.47 | 3.41 |
| 54 | 120–121 | C₁₉H₁₅ClN₂OS₂ | C | 58.98 | 3.91 |
|  |  |  | F | 58.46 | 4.07 |
| 55 | 165–166 | C₁₉H₁₅ClN₂O₂S₂ | C | 56.64 | 3.75 |
|  |  |  | F | 57.43 | 4.06 |

*C = Calculated
F = Found

TABLE 2

Diet Incorporated Screen % Kill (5% Formulation on Clay)

| Cmpd. No. | Exposure Period (days) | SAW 200 | SAW 20 | SAW 2 | Cl 200 | Cl 20 | Cl 2 |
|---|---|---|---|---|---|---|---|
| 1[b] | 1 | 0 | 0 | 0 | 0 | 0 | 0 |
|  | 6 | 90 | 90 | 0 | 50 | 10 | 0 |
|  | 9 | 100 | 100 | 40 | 80 | 10 | 0 |
| 2 | 1 | 0 | 0 | 0 | 0 | 10 | 0 |
|  | 3 | 0 | 0 | 0 | 20 | 20 | 20 |
|  | 8 | 0 | 10 | 40 | 20 | 40 | 20 |
| 3 | 1 | 0 | 0 | 0 | 10 | 0 | 0 |
|  | 4 | 60 | 0 | 0 | 10 | 0 | 0 |
|  | 8 | 60[d] | 20[d] | 0 | 10 | 0 | 0 |
| 4[b] | 1 | 0 | 0 | 0 | 0 | 0 | 0 |
|  | 6 | 90 | 90 | 0 | 30 | 10 | 0 |
|  | 9 | 90 | 100 | 10 | 60 | 20 | 0 |
| 5 | 1 | 0 | 0 | 0 | 0 | 0 | 0 |
|  | 5 | 70 | 0 | 0 | 30 | 0 | 10 |
|  | 8 | 90 | 10 | 0 | 30 | 10 | 40 |
| 6 | 4 | 0 | 0 | 0 | 30 | 0 | 0 |
|  | 8 | 10 | 0 | 0 | 10 | 40 | 0 |
| 7 | 1 | 0 | 0 | 0 | 0 | 0 | 0 |
|  | 3 | 0 | 0 | 0 | 70 | 0 | 0 |
|  | 8 | 0 | 0 | 0 | 70 | 0 | 0 |
| 8[c] | 1 | 0 | 0 | 0 | 0 | 0 | 0 |
|  | 2 | 30[d] | 0 | 0 | 0 | 0 | 0 |
|  | 8 | 40 | 0 | 0 | 60 | 0 | 0 |
| 9[c] | 1 | 0 | 0 | 0 | 0 | 0 | 40 |
|  | 3 | 30 | 0 | 0 | 0 | 0 | 40 |
|  | 8 | 100 | 60 | 0 | 70 | 20 | 40 |
| 10[c] | 1 | 0 | 0 | 0 | 0 | 0 | 0 |
|  | 5 | 90 | 20[d] | 20 | 20 | 10 | 0 |
|  | 8 | 90 | 40 | 20 | 20 | 20 | 0 |
| 11[b] | 1 | 0 | 0 | 0 | 0 | 0 | 0 |
|  | 3 | 90 | 10[d] | 20 | 10[e] | 0 | 0 |
|  | 8 | 90 | 30 | 20 | 40 | 0 | 0 |
| 12[b] | 1 | 0 | 0 | 0 | 0 | 0 | 0 |
|  | 3 | 30[d] | 0 | 0 | 0 | 0 | 0 |
|  | 9 | 40[d] | 0 | 0 | 80 | 30 | 0 |
| 13[b] | 1 | 0 | 0 | 0 | 0 | 0 | 10 |
|  | 4 | 70 | 0 | 90 | 0 | 0 | 10 |
|  | 7 | 70 | 0 | 100 | 0 | 0 | 10 |
| 14 | 1 | 0 | 0 | 0 | 0 | 0 | 0 |
|  | 3 | 0 | 0 | 0 | 0 | 0 | 0 |
|  | 8 | 60 | 10 | 0 | 20 | 0 | 0 |
| 15[b] | 1 | 0 | 0 | 0 | 0 | 0 | 0 |
|  | 6 | 70 | 20 | 0 | 20 | 0 | 0 |
|  | 9 | 90 | 80 | 0 | 50 | 10 | 0 |
| 16 | 1 | 0 | 0 | 0 | 10 | 0 | 0 |
|  | 3 | 80 | 80 | 0 | 40 | 20 | 0 |
|  | 8 | 100 | 100 | 80 | 50 | 50 | 20 |
| 17 | 1 | 0 | 0 | 0 | 0 | 0 | 0 |
|  | 4 | 50 | 0 | 0 | 0 | 0 | 0 |
|  | 7 | 60 | 10 | 0 | 40 | 20 | 10 |
| 18[b] | 1 | 0 | 0 | 0 | 0 | 0 | 0 |
|  | 6 | 0 | 10 | 0 | 30 | 10 | 0 |
|  | 9 | 40 | 40 | 0 | 30 | 10 | 0 |
| 19 | 1 | 0 | 0 | 0 | 0 | 0 | 10 |
|  | 4 | 70 | 20 | 0 | 0 | 0 | 10 |
|  | 8 | 80 | 50[d] | 0 | 0 | 0 | 20 |
| 20 | 1 | 0 | 0 | 0 | 0 | 0 | 10 |
|  | 4 | 100 | 100 | 50 | 40 | 0 | 10 |
|  | 8 | 100 | 100 | 90 | 80 | 20 | 10 |
| 21 | 1 | 0 | 0 | 0 | 0 | 0 | 10 |
|  | 4 | 100 | 60 | 20 | 20 | 0 | 10 |
|  | 8 | 100 | 80[d] | 20[d] | 70 | 10 | 10 |
| 22 | 1 | 0 | 0 | 0 | 10 | 10 | 0 |
|  | 6 | 100 | 80 | 90 | 70 | 20 | 0 |
|  | 9 | 100 | 100 | 90 |  |  |  |
| 23 | 1 | 20 | 0 | 0 | 0 | 0 | 0 |
|  | 3 | 20 | 20 | 0 | 50 | 20 | 10 |
|  | 8 | 100 | 30[d] | 20 | 100 | 100 | 80 |
| 24 | 1 | 0 | 0 | 0 | 0 | 0 | 0 |
|  | 3 | 20 | 0 | 0 | 0 | 0 | 0 |
|  | 8 | 100 | 0 | 0 | 0 | 10 | 0 |
| 25 | 1 | 0 | 0 | 0 | 0 | 0 | 0 |
|  | 3 | 100 | 90 | 0 | 0 | 0 | 0 |
|  | 8 | 100 | 90 | 30 | 0 | 20 | 0 |
| 26 | 1 | 0 | 0 | 0 | 0 | 0 | 0 |
|  | 3 | 70 | 0 | 0 | 0 | 0 | 0 |
|  | 8 | 70 | 0 | 0 | 20 | 0 | 0 |
| 27 | 1 | 0 | 10 | 0 | 0 | 0 | 0 |
|  | 7 | 100 | 80 | 10 | 80 | 20 | 0 |
| 28 | 4 | 80 | 10 | 10 | 70 | 30 | 0 |
|  | 8 | 90 | 20 | 10 | 100 | 80 | 30 |
| 29 | 1 | 0 | 0 | 0 | 0 | 0 | 0 |
|  | 3 | 90 | 0 | 0 | 70 | 100 | 0 |
|  | 8 | 90 | 0 | 0 | 100 | 100 | 10 |
| 30[c] | 1 | 0 | 0 | 0 | 0 | 0 | 0 |
|  | 5 | 100 | 90 | 0 | 0 | 0 | 0 |
|  | 8 | 100 | 90 | 20[d] | 40 | 0 | 0 |
| 31[c] | 1 | 0 | 0 | 0 | 0 | 0 | 0 |
|  | 3 | 90 | 10 | 0 | 0 | 0 | 0 |
|  | 8 | 100 | 90 | 20[d] | 40 | 0 | 0 |
| 32[c] | 1 | 0 | 0 | 0 | 0 | 0 | 0 |
|  | 5 | 100 | 100 | 40[d] | 10 | 0 | 10 |
|  | 8 | 100 | 100 | 40 | 30 | 20 | 10 |
| 33[b] | 1 | 0 | 0 | 0 | 0 | 0 | 0 |
|  | 3 | 100 | 20[f] | 0 | 0 | 10 | 0 |
|  | 8 | 100 | 50[d,f] | 0 | 30 | 10 | 0 |
| 34[b] | 1 | 0 | 0 | 0 | 0 | 0 | 0 |
|  | 3 | 60 | 0 | 0 | 10 | 0 | 0 |
|  | 10 | 90 | 10 | 0 | 60 | 30 | 0 |
| 35[b] | 1 | 0 | 0 | 0 | 0 | 0 | 0 |
|  | 4 | 100 | 80 | 70 | 0 | 0 | 0 |
|  | 7 | 100 | 90 | 90 | 30 | 0 | 0 |
| 36 | 1 | 40 | 0 | 0 | 0 | 0 | 0 |
|  | 3 | 70 | 10 | 0 | 0 | 0 | 0 |
|  | 8 | 100 | 90 | 0 | 100 | 30 | 0 |
| 37[b] | 2 | 0 | 0 | 0 | 10 | 0 | 0 |
|  | 3 | 0 | 0 | 0 | 10 | 0 | 0 |
|  | 5 | 0 | 0 | 0 | 10 | 10 | 0 |

TABLE 2-continued

Diet Incorporated Screen
% Kill
(5% Formulation on Clay)

| Cmpd. No. | Exposure Period (days) | SAW 200 | SAW 20 | SAW 2 | Cl 200 | Cl 20 | Cl 2 |
|---|---|---|---|---|---|---|---|
|  | 10 | 30 | 10 | 0 | 20 | 10 | 10 |
| 38[b] | 2 | 10 | 10 | 0 | 0 | 0 | 0 |
|  | 3 | 70 | 50 | 0 | 0 | 0 | 0 |
|  | 5 | 100 | 80 | 0 | 10 | 0 | 0 |
|  | 10 | 100 | 90 | 0 | 30 | 0 | 0 |
| 39[b] | 2 | 0 | 0 | 0 | 0 | 0 | 0 |
|  | 3 | 60 | 30 | 0 | 0 | 0 | 0 |
|  | 5 | 100 | 90 | 10 | 40 | 0 | 0 |
|  | 10 | 100 | 100 | 50 | 70 | 20 | 0 |
| 40 | 1 | 0 | 0 | 0 | 0 | 0 | 0 |
|  | 3 | 100 | 90 | 0 | 0 | 0 | 0 |
|  | 8 | 100 | 90 | 30 | 0 | 20 | 0 |
| 41 | 1 | 0 | 0 | 0 | 0 | 0 | 0 |
|  | 3 | 100 | 60 | 0 | 0 | 0 | 0 |
|  | 8 | 100 | 60 | 0 | 10 | 20 | 30 |
| 42 | 1 | 0 | 0 | 0 | 0 | 0 | 0 |
|  | 3 | 90 | 100 | 100 | 40 | 10 | 10 |
|  | 8 | 100 | 100 | 100 | 70 | 60 | 60 |
| 43[b] | 1 | 0 | 0 | 0 | 0 | 10 | 0 |
|  | 5 | 20 | 0 | 0 | 10 | 10 | 0 |
|  | 9 | 60 | 30 | 0 | 40 | 20 | 0 |
| 44 | 1 | 0 | 0 | 0 | 0 | 10 | 0 |
|  | 3 | 0 | 0 | 0 | 0 | 10 | 50 |
|  | 8 | 0 | 10 | 20 | 0 | 20 | 60 |
| 45 | 1 | 0 | 0 | 0 | 0 | 0 | 0 |
|  | 4 | 100 | 90 | 0 | 30 | 0 | 0 |
|  | 8 | 100 | 90 | 10 | 80 | 0 | 0 |
| 46 | 1 | 0 | 0 | 0 | 0 | 0 | 0 |
|  | 4 | 20 | 0 | 0 | 0 | 0 | 0 |
|  | 8 | 60 | 0 | 0 | 0 | 0 | 0 |
| 47[b] | 1 | 0 | 0 | 0 | 0 | 0 | 0 |
|  | 6 | 70 | 0 | 0 | 40 | 0 | 0 |
|  | 9 | 80 | 0 | 0 | 60 | 0 | 0 |
| 48 | 1 | 0 | 0 | 0 | 0 | 0 | 0 |
|  | 4 | 0 | 0 | 0 | 0 | 0 | 0 |
|  | 8 | 10[d] | 0 | 0 | 60 | 10 | 0 |
| 49 | 1 | 0 | 0 | 0 | 0 | 0 | 0 |
|  | 3 | 30 | 0 | 0 | 10 | 0 | 10 |
|  | 8 | 70[g] | 0 | 0 | 10 | 0 | 40 |
| 50[c] | 1 | 0 | 0 | 0 | 0 | 0 | 0 |
|  | 3 | 30 | 0 | 0 | 0 | 0 | 0 |
|  | 8 | 100 | 30[d] | 0 | 20 | 0 | 0 |
| 51[b] | 1 | 0 | 0 | 0 | 0 | 0 | 0 |
|  | 3 | 10[d] | 0 | 0 | 0 | 0 | 0 |
|  | 10 | 40 | 0 | 0 | 30 | 0 | 0 |
| 52[b] | 1 | 0 | 0 | 0 | 0 | 0 | 0 |
|  | 5 | 0 | 0 | 0 | 0 | 0 | 0 |
|  | 8 | 60[h] | 0 | 0 | 0 | 0 | 0 |
| 53[b] | 2 | 0 | 0 | 10 | 0 | 0 | 0 |
|  | 3 | 0 | 0 | 10 | 0 | 0 | 0 |
|  | 5 | 0 | 0 | 10 | 0 | 0 | 0 |
|  | 10 | 0 | 0 | 10 | 20 | 0 | 30 |
| 54[b] | 1 | 0 | 0 | 0 | 0 | 0 | 0 |
|  | 5 | 10 | 0 | 0 | 0 | 10 | 0 |
|  | 8 | 80 | 0 | 0 | 0 | 10 | 0 |
| 55[b] | 1 | 0 | 0 | 0 | 0 | 0 | 0 |
|  | 3 | 0 | 0 | 0 | 0 | 0 | 0 |
|  | 8 | 40 | 0 | 0 | 0 | 0 | 0 |
| 17 | | 70 | 20 | 0 | 0 | 0 | 0 |

[a]Insects
SAW = Southern armyworm (*Spodoptera eridania*)
Cl = Cabbage looper (*Trichoplusia ni*)
[b]20% Formulation on microcrystalline cellulose.
[c]5% Formulation on microcrystalline cellulose.
[d]SAW moribund with mottled appearance.
[e]CL moribund with punctured bodies.
[f]Larvae have exposed epidermis.
[g]Moribund, small larvae.
[h]Moribund two-headed larvae.

I claim:
1. A compound of the formula:

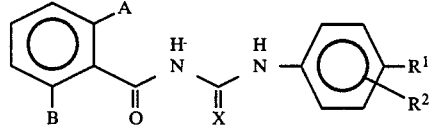

in which:
A. A is chloro, B is hydrogen, X is oxygen, and $R^1$ is

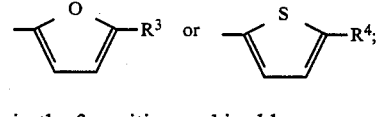

$R^2$ is in the 3-position and is chloro, cyano, alkyl of 1 or 2 carbon atoms, alkoxy of 1 or 2 carbon atoms, or is in the 3- and 5-positions and at each position is a halogen atom; $R^3$ is hydrogen or chloro; $R^4$ is hydrogen or methyl; or B. A is chloro, B is hydrogen, X is sulfur, and $R^1$ is

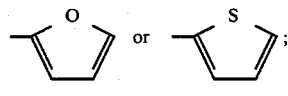

$R^2$ is cyano, alkyl of 1 or 2 carbon atoms, alkoxy of 1 or 2 carbon atoms, or halomethyl; or C. A and B are each fluoro, X is oxygen; and $R^1$ is

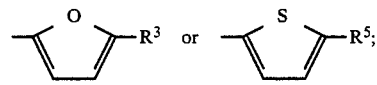

$R^2$ is in the 3-position and is hydrogen, halo, cyano, alkyl of 1 or 2 carbon atoms, alkoxy of 1 to 3 carbon atoms, halomethyl, halomethoxy, or is in the 3- and 5-positions and at each position is a halogen atom; $R^3$ is as defined above and $R^5$ is hydrogen, chloro, methyl, or trifluoromethyl.

2. An insecticidal composition comprising an insecticidal amount of the compound of claim 1 in admixture with a compatible vehicle.

3. A method for controlling insects which comprises applying to the locus where control is desired an insecticidal amount of the compound of claim 1.

* * * * *